United States Patent [19]

Ulrich et al.

[11] 4,433,677
[45] Feb. 28, 1984

[54] IMPLANTABLE SPLINT FOR CORRECTING LUMBOSACRAL SPONDYLODESIS

[75] Inventors: Max B. Ulrich, Amselweg 55, D-7900 Ulm; Heinrich Ulrich, Ulm, Fed. Rep. of Germany

[73] Assignee: Max Bernhard Ulrich, Ulm, Fed. Rep. of Germany

[21] Appl. No.: 383,175

[22] Filed: May 28, 1982

[30] Foreign Application Priority Data

May 29, 1981 [DE] Fed. Rep. of Germany ....... 3121272

[51] Int. Cl.³ .......................................... A61F 5/04
[52] U.S. Cl. ................................... 128/69; 128/92 B; 128/92 R
[58] Field of Search ................. 128/69, 92 B, 92 C, 128/84 C, 92 R

[56] References Cited

U.S. PATENT DOCUMENTS 4,175,555  11/1979  Herbert ............................ 128/92 B

FOREIGN PATENT DOCUMENTS 227510  2/1969  U.S.S.R. ............................... 128/69

OTHER PUBLICATIONS

Zimmer Catalog, 1973, p. D67, Fig. 10, Warsaw, Ind. 46580.

*Primary Examiner*—C. Fred Rosenbaum
*Assistant Examiner*—C. W. Shedd
*Attorney, Agent, or Firm*—Karl F. Ross; Herbert Dubno

[57] ABSTRACT

A spinal distraction splint has two like anchor screws extending along respective longitudinal screw axes and adapted to be anchored in the pelvis with the axes crossing. Each of the screws has a head formed with a transversely open recess centered on a respective transverse axis and with an annular array of teeth centered on and angularly equispaced about the respective transverse axis. A bolt extends through one of the recesses and is threaded in the other recess. Thus the bolt secures the heads together with the transverse axes coaxial and the teeth interengaged. Respective distraction rods each have one end braced on the respective screw and another end braced oppositely against a vertebra. Once the two anchor screws are properly inserted and then their heads are locked together the interfitting teeth on the heads absolutely locks them against angular rotation relative to each other about the axis of the fastener bolt and all other relative motion is eliminated by the clamping action of this bolt.

6 Claims, 5 Drawing Figures

IMPLANTABLE SPLINT FOR CORRECTING LUMBOSACRAL SPONDYLODESIS

FIELD OF THE INVENTION

The present invention relates to an implantable spinal splint. More particularly this invention concerns such a splint which is used to correct lumbosacral spondylodesis.

BACKGROUND OF THE INVENTION

An implantable spinal splint for treating lumbosacral spondylodesis has a pair of anchor rods seated in the ilia and extending at angles to each other with their outer ends juxtaposed. An appropriately angled connector interconnects these two ends so they form a rigid platform against which two distraction rods or braces are propped. The other ends of these braces are engaged under the rear processes of a lower-back vetebra to urge them up, thereby bending the upper spine portion forward.

Due to the considerable variation in pelvis size and shape, the angle at which the two anchor screws extend relative to each other varies through a wide range. Thus it is necessary for the surgeon to carry a stock of angled couplings for all the entire range of positions. If screw diameter varies, it is also necessary to carry the full range of angular sizes in each different diameter.

OBJECTS OF THE INVENTION

It is therefore an object of the present invention to provide an improved implantable spinal splint.

Another object is the provision of such an implantable spinal splint which overcomes the above-given disadvantages.

Yet another object is to provide a spinal splint which is adjustable but which when tightened is extraordinarily rigid and resistant to loosening.

SUMMARY OF THE INVENTION

These objects are attained according to the instant invention in a spinal distraction splint having two like anchor screws extending along respective longitudinal screw axes and adapted to be anchored in the pelvis with the axes crossing. Each of the screws has a head formed with a transversely open recess centered on a respective transverse axis and with an annular array of teeth centered on and angularly equispaced about the respective transverse axis. A bolt extends through one of the recesses and is threaded in the other recess. Thus the bolt secures the heads together with the transverse axes coaxial and the teeth interengaged. Respective distraction rods each have one end braced on the respective screw and another end braced oppositely against a vertebra.

Thus with the system of the instant invention, the two anchor screws are properly inserted and then their heads are locked together. The use of interfitting teeth on the heads absolutely locks them against angular rotation relative to each other about the axis of the fastener bolt and all other relative motion is eliminated by the clamping action of this bolt. The teeth are relatively fine, normally allowing about 10° offset between adjacent locking positions, so that the system can fit any size or shape pelvis.

According to this invention the other recess is threaded and the one recess is tapered and the bolt has a complementarily tapered head. The threaded connection obviously is very strong. Once the bolt is torqued tight, its frustoconical head will lie in all-around surface contact with the interior of the respective recess, so that an extremely tight connection is made, one that is very resistant to loosening.

The screws of the instant invention are formed around the respective heads with seats centered on the respective transverse axes and perfectly complementary to the outer surface of the head of the other screw. These heads and seats are generally cylindrical and centered on the respective transverse axes. Their surfaces also are in tight intimate contact with each other once the sacral-rod assembly is tightened so that the two screws are snugly secured against any type of motion relative to each other.

The bolt according to the invention has a head formed with an actuation recess of polygonal section. Thus it can be tightened with an allen or hex wrench.

DESCRIPTION OF THE DRAWING

The above and other features and advantages will become more readily apparent from the following, reference being made to the accompanying drawing in which.

SPECIFIC DESCRIPTION

Figure 1:
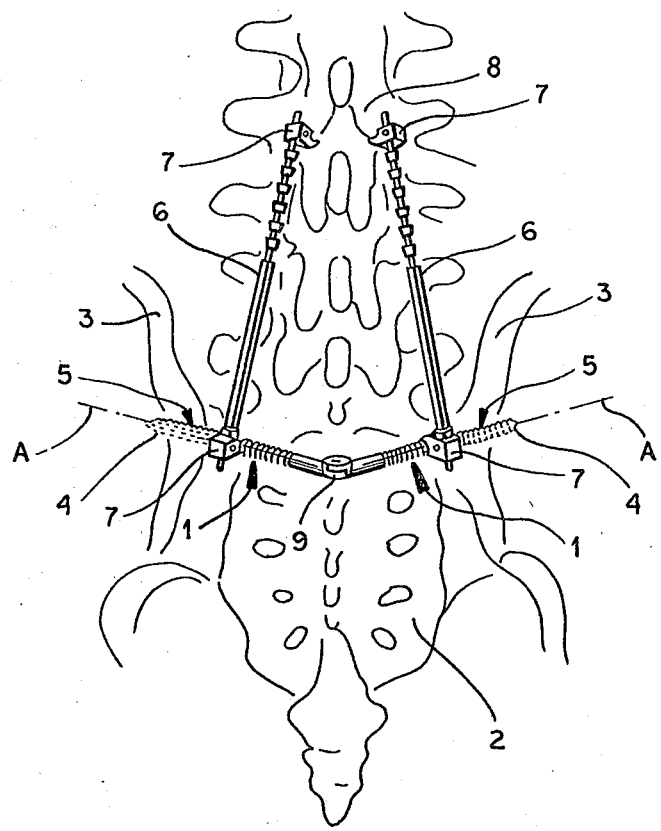
FIG. 1 is a rear side view of the implanted splint according to this invention.
Figure 2:
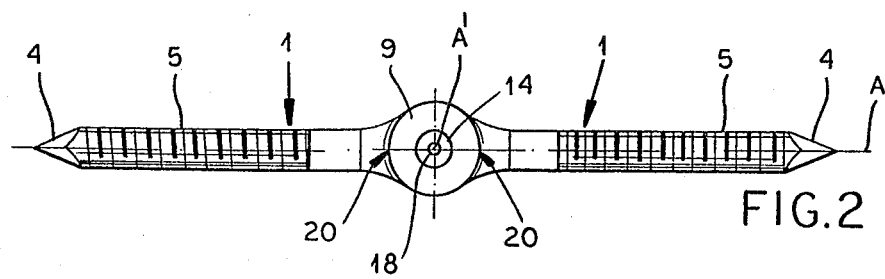
FIG. 2 is a top view of the anchor-screw assembly according to this invention.
Figure 3:
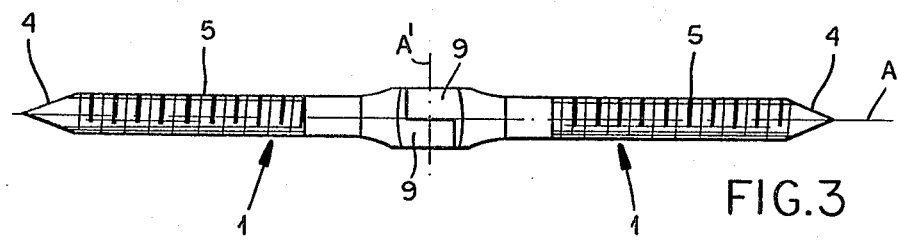
FIG. 3 is a side view of the assembly of FIG. 2.
Figure 4:
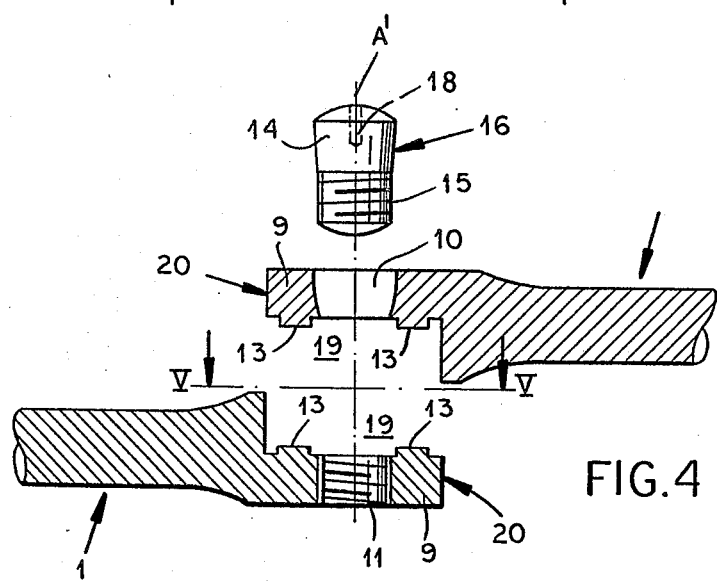
FIG. 4 is an axial section through the central part of the assembly as seen in FIG. 3, but in exploded view.
Figure 5:
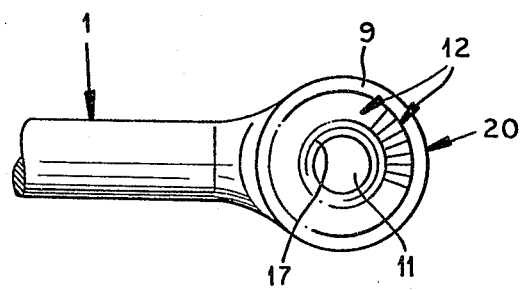
FIG. 5 is a view taken along the plane V—V of FIG. 4.

As seen in FIG. 1 an implant for treating lumbosacral spondylodesis has two like sacral screws or rods 1 anchored in the ilia 3 at the back of the pelvis 2, symmetrical with the skeletal symmetry plane. To this end these rods 1 have pointed ends 4 and are formed with screwthreads 5. They are centered on respective axes A that cross at an obtuse angle at the skeletal symmetry plane and are there connected together at heads 9 and 9'.

Braced between each of the rods 1 and a lower-back vertebra 8 is a distraction rod 6 having hooks 7 on its ends, one hook 7 engaging under the rearward bony process of the vertebra 8 and the other hook 8 engaged over the respective screw 1. These rods 6 are of adjustable length between their hooks or anchors 7 and may even be of two-part telescoping construction with the two parts threaded together so that relative rotation steplessly varies length. These rods 6 may also be constructed along the lines described in my copending patent application No. 383,169 filed May 28, 1982.

As better seen in FIGS. 2-5 the two screws 1 are like but not identical. Their heads 9 and 9' are externally complementarily shaped, each having a part-cylindrical seat 19 centered on a transverse axis A' perpendicular to the respective axis A and a complementary part-cylindrical outer surface 20 fittable with the seat 19 of the other screw 1 with the axes A' coaxial. In addition, the head 9 is formed with a frustoconically tapered recess or passage 10 and the other head 9' with a screwthread recess or passage 11, both centered on the axes A'. In addition around each of the passages 10 and 11 there is an axially centered annular array 12 of thirty-six teeth 13 that determine a multiplicity of 10°-offset positions for the two screws 1 relative to each other about the coaxial axes A'.

The two complementary heads 9 and 9' are secured together by a locking bolt 16 having a threaded shank 15 that engages fully in the threaded passage 11 and a frustoconical head 14 complementary to the passage 10. The screw 19 also has a hexagonal recess 18 in its head 14 so it can be tightened by an allen wrench or hex key.

When the screw or bolt 16 is driven home it locks the two screws 1 together into a single very rigid assembly. The complementary head 14 and recess 10 will interfit in surface contact once the two heads 9 and 9' have interfit with the teeth 13 of one engaging between the teeth 13 of the other, the surfaces 19 and 20 juxtaposed, and the axes A' coaxial. The parts therefore virtually all fit together in extensive surface contact. If of normal metallic construction they can be counted to freeze molecularly or cold weld to each other.

Thus the assembly according to this invention provides an extremely rigid platform for the distractor rods 6, so that these rods can exert considerable forces. At the same time the use of two joinable rods 1 allows the orthopedic surgeon to operate without having to have on hand a large stock of variously angled couplings.

I claim:

1. A spinal distraction splint comprising:
   two like anchor screws extending along respective longitudinal screw axes and adapted to be anchored in the pelvis with said axes crossing, each of said screws having a head formed with a transversely open recess centered on a respective transverse axis and with an annular array of teeth centered on the respective transverse axis;
   a bolt extending through one of said recesses and threaded in the other recess, said bolt securing said heads together with said transverse axes coaxial and said teeth interengaged; and
   respective distraction rods each having one end adapted to be braced on the respective screw and another end adapted to be braced oppositely against a vertebra.

2. The splint defined in claim 1 wherein said one recess is tapered and said bolt has a complementarily tapered head.

3. The splint defined in claim 1 wherein said screws each extend from a respective head; each said head having a respective seat centered on the respective transverse axis which is perfectly complementary to the head of the other screw.

4. The splint defined in claim 3 wherein said heads and seats are generally cylindrical and centered on the respective transverse axes.

5. The splint defined in claim 1 wherein said bolt has a head formed with an actuation recess of polygonal section.

6. The splint defined in claim 1 wherein said teeth are angularly equispaced about the respective transverse axes.

* * * * *